United States Patent [19]
Studer

[11] 3,936,373
[45] Feb. 3, 1976

[54] FECAL EXAMINATION DEVICE

[76] Inventor: Arnold David Studer, P.O. Box 5, West Grove, Pa. 19390

[22] Filed: July 2, 1975

[21] Appl. No.: 592,495

Related U.S. Application Data

[63] Continuation-in-part of Ser. No. 525,231, Nov. 19, 1974, abandoned, and a continuation of Ser. No. 528,585, Nov. 29, 1974, abandoned.

[52] U.S. Cl. ............... 209/17; 209/173; 23/230 B; 23/292
[51] Int. Cl.² ................................................ B03B 5/36
[58] Field of Search ......... 209/2, 3, 5, 17, 162, 163, 209/172, 173, 250, 273, 268, 269, 305, 306, 397, 399, 273; 210/358, DIG. 24, 359, 402, 453–455, 469, 474, 475, 515, 516, 518; 220/371, 372; 23/230 B, 292

[56] References Cited
UNITED STATES PATENTS

| | | | |
|---|---|---|---|
| 795,774 | 7/1905 | Jones | 210/358 |
| 2,258,524 | 10/1941 | Vigurs | 210/474 X |
| 3,370,925 | 2/1968 | Trueblood | 23/292 |
| 3,488,768 | 1/1970 | Rigopulos | 210/455 X |
| 3,819,045 | 6/1974 | Greenwald | 209/17 |

FOREIGN PATENTS OR APPLICATIONS

| | | | |
|---|---|---|---|
| 10,763 | 8/1887 | United Kingdom | 210/469 |

*Primary Examiner*—Frank W. Lutter
*Assistant Examiner*—Ralph J. Hill
*Attorney, Agent, or Firm*—Rollin D. Morse

[57] ABSTRACT

A filter thimble adapted for use in a float-or-sink process of separating ova from samples of feces contained in standarized transport receptacles has an outside diameter of about ¾ that of the inside of the receptacle, has a bottom, has an open top, has around its upper side surface a closure operatively fittable to the transport receptacle, and around its lower side surface numerous perforations of dimension only several times larger than the ova. The under surface of the closure is frusto-conical, with smaller end up and fitted liquid-tight to the outside of the thimble, and several of the perforations have their outer openings immediately below the point of fit.

5 Claims, 1 Drawing Figure

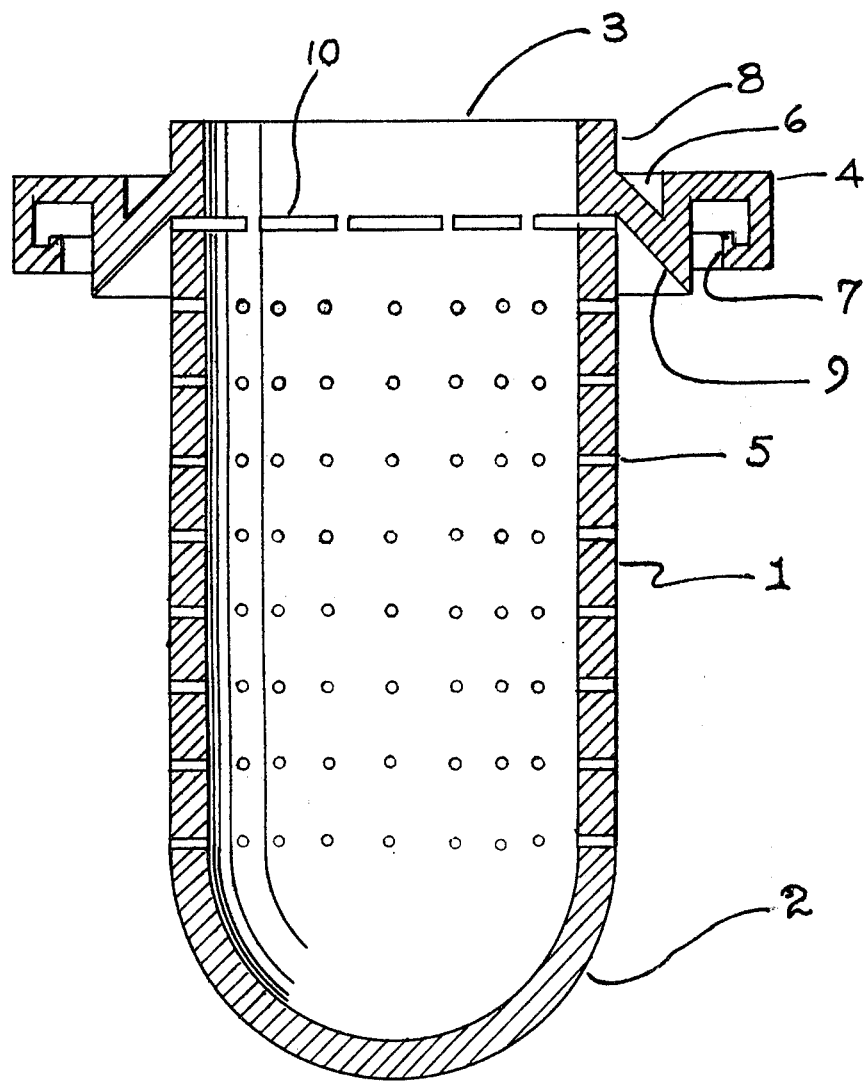

FECAL EXAMINATION DEVICE

REFERENCE TO EARLIER APPLICATION

This application is a continuation in part of application Ser. No. 525231 filed Nov. 19, 1974 and continuation of application Ser. No. 528585 filed Nov. 29, 1974, in the name of Arnold David Studer, each now abandoned.

BACKGROUND OF THE INVENTION

The present invention relates to means and method for examining fecal matter to determine the presence of ova or eggs of parasites such as might be found in the fecal matter. Especially when the infestation is small, and also with some variations in the physical condition of feces, it is important that a good separation of ova from the feces be obtained. And at the same time it is highly desirable that the steps in preparing the feces samples, malodorous and esthetically upleasant at unpleasant shall be made as few, as simple, and as non-contaminating to the technician and the laboratory as possible. Obviously, it is desirable that the receptacles and auxiliary apparatus be disposable after one use in order to avoid the unpleasantness of clean-up. Yet, for a laboratory handling many samples each day, as is common in active veterinary hospitals, disposable apparatus must not only cost very little, but must be environmentally acceptable. In the present marketplace, these considerations and others clearly dictate that the apparatus shall be of inexpensive plastic such as polyethylene, and shall have the least possible number and complexity of components.

For many years the preferred laboratory technique, in numerous minor variations, has been the use of a float-or-sink process, in which a liquid of density between that of the ova and that of the other fecal matter is stirred into the feces sample, and opportunity is provided for the ova to separate by flotation from the other matter. The ova, having floated to the top of the liquid, are then transferred to a microscope slide, as by touching the cover glass to the surface of the liquid. Under the microscope the kinds of ova can be discerned, and the seriousness of the infestation estimated by rough counting of the number of each kind of ova seen in the field.

This prior art process has been improved in several ways, but still suffers several problems, not only esthetic, but also of a degree of unreliability or inaccuracy.

Older improvements were (1) Centrifuging the float-or-sink mixture to achieve a sharp separation. (2) Filtering the float-or-sink mixture from the mixture receptacle into another receptacle by pouring the mixture through a strainer, and both metallic and non-metallic strainers have been used. Movement through the strainer is by gravity. In the second receptacle the ova, largely freed from the other fecal matter, float to the top, and are transferred as before mentioned, to a microscope slide cover glass. Pertinent references are:

COLES, E. H. "Veterinary Clinical Pathology," W. B. Saunders Co., Philadelphia, 1967, pg 332

CHANDLER, A. C. "Introduction to Parasitology" 8th Ed., John Wiley & Sons, N.Y. 1949, pg 249 – 251

BODDIE, G. F. "Diagnostic Methods in Veterinary Medicine," Lippincott, Philadelphia, 1953, pg 309

HOSKINS, H. P. et al, Ed., "Canine Medicine" American Veterinary Publications, Inc., Santa Barbara, California, 1959, pg 605, 606.

Such methods are described in a most recent improvement, which is disclosed in U.S. Pat. No. 3,819,045 issued in June 25, 1974 to Robert J. Greenwald, in which is disclosed a combination of apparatus elements, including a shallow cup means for original receipt of feces sample, a cover means for use during transport of the sample to laboratory, an open tube means for thrusting into said cup means whereby to extend it vertically and to form a treatment receptacle, a piston means of diameter to fit snugly into said tube, the piston having its face perforated, and having a piston-rod-like handle extending axially. In use, at the laboratory, the transport cover is removed from the shallow cup, the open tube is thrust into the well of the cup around the feces, the tube is partially filled with the float-or-sink liquid diluent, the feces and the diluent are mixed together using a wooden stick supplied with the kit, the piston, held by its handle, is inserted into the open top of the cup and pressed downward compressing much of the feces material as a cake on the bottom face of the piston, while the liquid and some of the ova pass through the perforations of the piston into the space above. The length of the piston's handle is short enough that when the piston "bottoms," the top of the handle is entirely inside the receptacle. If the volume of the original feces sample and of the added diluent were not too great, the top of the handle is not quite submerged in the mixture and the finger of the operator is not contaminated. Additional diluent is then added to fill the tube barely to over-flowing, forming a meniscus at the top into which the ova from the space above the piston collect within a few minutes. By laying a microscope slide cover glass on the meniscus, a drop of liquid with its collected ova is picked up, and under the microscope the number and kind of ova can be visually determined.

SUMMARY OF THE INVENTION

The present invention has for some of its objects the following:

1. A major reduction in the number of special component parts, while utilizing standardized commercial mass-produced transport receptacles not only for transport but also for sample treatment.

2. A large improvement in the degree of separation of ova from other fecal material, whereby a true estimate may be made of the seriousness of the infestation in the animal from which the feces were obtained.

These objects and others are obtained by the present invention, in which there is provided a thimble for use as a component in a fecal examining system in which feces samples to be examined for presence of ova are supplied in standardized transport receptacles of fixed predetermined dimensions, the thimble comprising an open-top generally cylindrical tube with a bottom, the tube having outside cross section approximately one half of the transport receptacle's cross section and carrying around its upper side surface a closure adapted to operatively close the top of the transport receptacle upon insertion of the thimble into the transport receptacle, and bearing around its lower side surface a screening means with numerous perforations with minimum dimension only several times larger than the said ova. The under surface of the closure is frustoconical, with smaller end up and fitted liquid-tight to the outside of the thimble, and several of the perforations have their outer openings immediately below the point of fit.

The method in the present invention is a fecal examining process for detecting the presence of ova in feces supplied in a standardized transport receptacle by float-or-sink separation of ova from other fecal material, comprising (a) providing a liquid diluent of specific gravity intermediate the ova and the other fecal material, and (b) providing an open-top thimble of cross-sectional area approximately one half the cross-sectional area of the transport receptacle, said thimble provided with numerous perforations in its lower side surfaces of dimension only several times larger than the ova, said thimble carrying around its upper side surface a closure for the said transport receptacle, said closure having a a frusto-conical under surface with smaller end up, whereby to guide any rising ova inwardly through adjacent perforations to the inside of the thimble, (c) forming a mixture of the feces within the transport receptacle with liquid diluent, (d) lowering the thimble under its own weight into the said mixture, while permitting ova to infiltrate into the thimble, (e) closing the transport receptacle with the closure of the thimble, (f) adding of liquid diluent in sufficient quantity to slightly overfill the thimble, whereby a meniscus of liquid is formed at the surface to which the infiltrated ova ascend.

DETAILED DESCRIPTION

In the single FIGURE the preferred thimble of this invention is shown in vertical cross section.

The tubular thimble 1 is closed at its bottom 2, a round bottom being shown, although a flat bottom would also suffice. The top of the thimble at 3 is open. Surrounding the upper part of the tubular wall is a closure 4, attached firmly or molded integrally with the upper part of the thimble as at 8. The outer portion of the closure is adapted to mate with a standardized transport receptacle not shown, such as a plastic vial of cylindrical shape as is conventional in the pharmaceutical trade. For the particular closure shown in the FIGURE, the vial or receptacle to which the closure is to be fitted may be a standard 4 to 9 dram plastic vial, which is ordinarily supplied by its manufacturers with a plastic snap cap. For this closure, the inside of the lower lip is turned inwardly and upwardly as shown at 7, in the same form as that of the plastic snap cap. Thereby, if the thimble with its closure be inserted in such a receptacle and pressed down firmly its closure will snap around the mouth of the receptacle and seal the junction securely. No novelty is claimed as to this method of sealing.

It is most desirable that a large annular clearance exist between the inside of the transport receptacle and the outside of the thimble. Preferably the cross-sectional area inside the thimble should approximately equal the annular cross-sectional area, and this relationship is achieved by making the outside diameter of the thimble of about ¾ the inside diameter of the receptacle. This large clearance is desirable in order to provide ample room for other fecal material to be suspended without packing.

It will be obvious that should receptacles of other top shape have been desired, for example, screw-top, the thimble closure could have been shaped and fabricated with gasket to mate with and seal such a screw-top. Likewise, the closure could have been so elementary as a cork with a hole in it, into which the tubular thimble was thrust.

An additional convenience in the use of the thimble is provided by making the top annular surface 6 of the closure concave, whereby an annular recess is formed around the top of the thimble large enough to hold several drops of overflow from the thimble top.

The lower side walls of the thimble are provided with a screening means comprising preferably numerous holes 5 of dimension only several times larger than the ova. Round holes about 1 to 1.5 mm in diameter spaced apart about 1.5 mm and covering the majority of the surface have been found very satisfactory. Other shapes of holes, extending even to horizontal or vertical slits, would also be satisfactory, as long as their smaller dimension will pass the ova while retaining the majority of the fibrous or other fecal matter.

The material of construction of the thimble is not critical. For low-cost thimbles disposable by incineration as would likely be applied to the disposal of the receptacle, molded polyethylene is entirely satisfactory.

For a thimble 0.6 in O.D. by 1.0 in. high below the closure, 10 circular rows each containing about 19 holes cover the entire cylindrical surface.

An improvement of the invention relates to the shape of the bottom side of closure, relative to the adjacent wall of the thimble. I have realized that a need exists to guide those ova which float to the surface of the annular space between thimble and receptacle to the perforations in the wall of the thimble, and also that perforations must be provided as high as possible, next to the under side of the closure, so that the ova can float from the annular collection region through the thimble perforations into the thimble interior.

The above need is answered by shaping the bottom side of the closure at 9 in a form called generally "frusto-conical," with small end up, and by providing a set of thimble perforations 10 as close as possible to the junction of the cone with the thimble; thereby, ova are guided by the frusto-conical surface, (which acts as a nozzle) into the perforations 10, and such ova add to those that had already permeated the lower levels of perforations as at 5.

While the surface 9 on the under side of the closure 4 is shown as frusto-conical in the FIGURE, and is so termed generically, it should be understood that this term also includes in addition to the true conical surface, other upwardly converging surfaces, such as bell-shape and such as portion of spherical surfaces, the important need being that the surface act as a nozzle to guide the ova toward the top most layer of perforations 10 in the thimble.

In the FIGURE the perforations 10 are shown as slits, which taken all together occupy nearly all the periphery of the thimble at their level, the walls between the ends of the adjacent slits being as thin as practical, whereby to provide the maximum amount of passageway for ova, while still limiting the passage of other fecal material. The vertical width of these slits, as in the perforations below, should be larger than the ova, but not more than 1 to 1.5 mm., in order to limit the flow of other fecal material.

While slits are preferred at this top level of perforations, round holes or other equivalent perforations are permissible if closely spaced.

The perforations 5 shown on the lower levels in the FIGURE are round holes, but as previously explained, may also be slits, either around the periphery as the perforations 10, or vertically. Or they may have other shapes, this feature not being critical.

A practical commercial design is provided as above described, but it is also possible and effective to use a thimble-shaped screen of woven or punched metal or plastic, adhered to the bottom of the upper tubular part of the thimble. Likewise, the lower part could be made as an open-work skeleton of plastic, covered with a tube of screen material.

USE OF THE THIMBLE

The thimble of this invention is used with the standardized transport receptacle in which the feces sample is brought to the laboratory. Normally the sampler will have been requested to put in enough sample only to occupy about 1/10 of the receptacle's depth. In the laboratory, any excess is removed and discarded, using a throw-away wooden or plastic spatula, and an amount of flotation liquid added to the receptacle to raise the level in it to about ¾ of the height — this is about ½ inch below the top of a standard 7-dram receptacle.

The flotation liquid may be any of the many prior art liquids, one example of which is sodium nitrate dissolved in water to an extent to have a specific gravity of 1.200. Low viscosity liquids are preferable, in order not to hinder the flotation of the ova.

After the liquid has been added to the sample in the transport receptacle, its cap is replaced and the capped receptacle thoroughly shaken to mix the liquid with the sample. The cap is then removed, and may be discarded.

The thimble of the invention is now inserted into the top of the transport receptacle, and allowed to settle under its own weight into the mixture. As this settling is taking place, the mixture is rising in the annular space between the inside of the receptacle and the outside of the thimble. As each of the sets of perforations becomes submerged, flotation liquid and ova from the mixture pass into the inside of the thimble, but because the submergence rate is low and under only slight pressure, no appreciable cake of other fecal material forms against the perforations, and free access is maintained for ova to pass into the thimble.

When the thimble has reached the bottom of its free fall, the technician operator presses the thimble's closure into engagement with the top of the receptacle, sealing the junction, and then adds additional flotation liquid into the thimble to raise the level to the open top of the thimble, and to form a slight meniscus. Any slight excess falls into the annular recess 6 of the thimble's closure.

After a wait of several minutes (preferably 9 –10 minutes) during which ova, both some of those still in the mixture and those already in the thimble, may rise into the meniscal surface of the flotation liquid, the technician lays a microscope cover glass upon the meniscal surface, thereby picking up surface liquid and the entrained ova. Placed on a slide and viewed under a microscope at 100 power, the ova of various parasites will be visible, and the field will be nearly free of other fecal material.

It is to be understood the foregoing detailed description and experimental verification are given merely by way of illustration, and that numerous variations may be made without departing from the spirit of the invention.

EXPERIMENTAL RESULTS

A series of tests has been carried out in the laboratory of a practising veteranarian, to compare the results obtained from the Greenwald System as described in U.S. Pat. No. 3,819,045 and the device of the present invention.

EXPERIMENTAL OBSERVATIONS

Feces from Cat with moderate infestation

| TEST | ROUND WORM OVA (Toxocara Species) | HOOK WORM OVA (Strongyle Species) |
| --- | --- | --- |
| METHOD | | |
| This Invention | 75, 75, 57* | 42* |
| Greenwald | 48, 70, 23 | 40 |

Feces from Dog with low to moderate infestation

| | Round Worm Ova | Hook Worm Ova | Whip Worm Ova |
| --- | --- | --- | --- |
| This Invention | 17, 5 | 33 | 17 |
| Greenwald | 15, 5 | 32 | 9 |

Two Sample Feces from Dogs with heavy infestations WHIP WORM OVA

| | Sample 1 | Sample 2 |
| --- | --- | --- |
| This Invention | 59 | 250 |
| Greenwald | 39 | 75 |

*The numbers in the table above are the count of ova within the microscope field at 100X, over the entire area of a standard cover glass, ¾ inch square.

What is claimed is:

1. A fecal examining process for detecting the presence of ova in feces supplied in a standardized transport receptacle by float-or-sink separation of ova from other fecal material, comprising (a) providing a liquid diluent of specific gravity intermediate the ova and the other fecal material, and (b) providing an open-top thimble of cross-sectional area approximately one half the cross-sectional area of the transport receptacle, said thimble provided with a screening means with numerous perforations in its lower side surfaces of dimension only several times larger then the ova, said thimble carrying around its upper side surface a closure for the said transport receptacle, (c) forming a mixture of the feces within the transport receptacle with liquid diluent, (d) lowering the thimble under its own weight into the said mixture, while permitting ova to infiltrate into the thimble, (e) closing the transport receptacle with the closure of the thimble, (f) adding of liquid diluent in sufficient quantity to slightly overfill the thimble, whereby a meniscus of liquid is formed at the surface to which the infiltrated ova ascend.

2. In apparatus for the sink-or-float separation of ova from feces contained in a transport receptacle, a filter thimble combined with receptacle closure means for said transport receptacle, the closure means having a top face and a bottom face, the thimble comprising an open-top, generally cylindrical tube with a bottom face, the tube carrying below its open top around its upper side surface the said closure means, and bearing around its lower side surface below said closure means a screening means permitting passage of said ova while retaining larger feces components, the top face of said closure means carrying an annular concave recess surrounding said tube.

3. In apparatus for use in the sink-or-float separation of ova from feces contained in a transport receptacle, a filter thimble combined with receptacle closure means, the closure means having a top face and a bottom face, the thimble comprising an open top, generally cylindrical tube with a bottom face, the tube carrying below its open top around its upper side surface the said closure means, the said closure bottom face having an upwardly converging surface, the said tube bearing around its lower side surface screening means including perforations at the junction of the said converging surface with said tube.

4. The filter thimble of claim 3, in which the upwardly converging surface on the bottom face of the closure is generally frusto-conical in section.

5. The filter thimble of claim 4, in which the perforations at the junction of the said converging surface with said tube are circumferentially arranged slits occupying the majority of the circumference.

* * * * *